United States Patent
Ripley et al.

(10) Patent No.: US 6,852,756 B1
(45) Date of Patent: Feb. 8, 2005

(54) USE OF PLEUROMUTILIN DERIVATIVES FOR TRANSDERMAL TREATMENT OF BACTERIAL DISEASES

(75) Inventors: Paul Howard Ripley, Tonbridge (GB); Erich Zeisl, Jenbach (AT); Stefan Horkovics-Kovats, Worgl (AT)

(73) Assignee: Novartis Animal Health US Inc., Greenboro, NC (US)

( * ) Notice: Subject to any disclaimer, the term of this patent is extended or adjusted under 35 U.S.C. 154(b) by 0 days.

(21) Appl. No.: 10/130,649

(22) PCT Filed: Nov. 20, 2000

(86) PCT No.: PCT/EP00/11519

§ 371 (c)(1),
(2), (4) Date: May 21, 2002

(87) PCT Pub. No.: WO01/37828

PCT Pub. Date: May 31, 2001

(30) Foreign Application Priority Data

Nov. 22, 1999 (EP) .............................................. 99123095

(51) Int. Cl.$^7$ ........................ A01N 37/02; A61K 31/22; A61K 31/70
(52) U.S. Cl. ......................................... 514/550; 514/25
(58) Field of Search ................................... 514/25, 550

(56) References Cited

U.S. PATENT DOCUMENTS

| | | | |
|---|---|---|---|
| 3,716,579 A | * | 2/1973 | Knauseder et al. |
| 4,096,262 A | | 6/1978 | Andrews et al. |
| 4,675,330 A | * | 6/1987 | Berner et al. ............... 514/365 |
| 5,578,585 A | * | 11/1996 | Matous et al. ................. 514/58 |
| 6,130,250 A | * | 10/2000 | Burch et al. ................. 514/550 |

FOREIGN PATENT DOCUMENTS

| | | |
|---|---|---|
| WO | WO 98/01127 | 7/1997 |
| WO | WO 99/51219 | 4/1999 |

OTHER PUBLICATIONS

Yiannos Contrafouris, Interscience Conference on Antimicrobial Agents and Chemotherapy—39th Meeting (Part VII), Sep. 26–29, 1999, Sann Francisco, Calif.*
European Agency for the Evaluation of Medicianl Products Veterinary Mediciens and Information Technology Unit, Committee for veterinary Medicinal Products: Tiamulin—Summary Report (1), EMA/MRL/578/99–Final, Aug. 1999.*
Berry et al. (Contrafouris et al.) "Pleuromutilins: a new approach to resistant S. aureus skin infections?", presented at ICAAC —39th meeting Sep. 28, 1999, San Francsisco, Ca.*
Europen Search Report.
Satterfield et al., "In Vivo Efficacy of the Novel Topical Pleuromutilins, SB–247386 and SB –268091", Intersci Conf Antimicrob Agents Chemother, vol. 39, No. 377, Sep. 26–29 (1999) (abstract No. 1804).

* cited by examiner

*Primary Examiner*—James O. Wilson
*Assistant Examiner*—Traviss C. McIntosh, III
(74) *Attorney, Agent, or Firm*—John Kung; David L. Marks

(57) ABSTRACT

Described is a method for transdermally controlling a bacterial infection in a non-human animal which comprises the step of topically applying to the non-human animal a medicament comprising valnemulin in free base or a pharmaceutically acceptable salt form.

9 Claims, No Drawings

USE OF PLEUROMUTILIN DERIVATIVES FOR TRANSDERMAL TREATMENT OF BACTERIAL DISEASES

The present invention relates to pleuromutilin and valnemulin derivatives. More concretely, it concerns for the manufacture of a medicament for the transdermal treatment of bacterial infections in humans and animals comprising a compound of the formula I as defined below. Said medicament is used in the prophylaxis or therapy of systemic bacterial infections, preferably infections in hoofed animals such as digital dermatitis (stable footrot), digital pododermatitis (chronic inflammation between the toes; footrot), and digital necrobacillosis (digital phlegmon, foul-in-the-foot, clit-ill etc.).

One preferred embodiment of the present invention is the cutaneous application of a compound of the formula I for systemic or remote effect

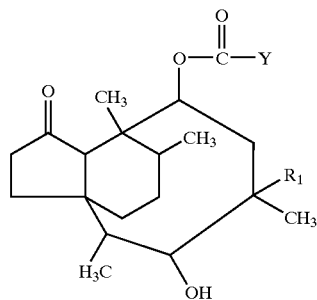

(1)

wherein $R_1$ ethyl or vinyl;
Y represents one group selected from COOH, —$CH_2$—$R_2$, and

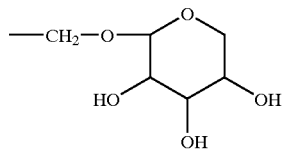

$R_2$ is H, halogen, OH, $NH_2$, SCN, $N_3$, COOH, C(S)S-[$C_{1-5}$alkyl], —S-pyridyl, —S-pyridyl substituted by one or two hydroxyl groups, $C_{1-5}$alkylthio, $C_{1-5}$alkylthio subsituited by one or more amino, hydroxyl or carboxyl groups, —O—$SO_2$-(4-methylphenyl), —S—$(CH_2)_m$—X, —$(CH_2\text{-Z})_r$-$(CH_2)_s$-Q or —S—$C(CH_3)_2$—$CH_2$—NH—C(O)-Q; or —S—$C(CH_3)_2$—$CH_2$—NH—C(O)—CH($NH_2$)—CH($CH_3$)$_2$;

X is a saturated or unsaturated 5- to 6-membered heterocyclic ring which is bound to the —S—$(CH_2)_m$— group through a carbon atom and which contains one or more heterogroups selected from the group consisting of O, S, N or —N($R_3$); whereby said heterocyclic ring is unsubsituited or mono- or poly-substituted by one or more substituents selected from the group consisting of halogen, hydroxy, mercapto, $C_{1-5}$alkyl, $C_{1-5}$alkanoyl, $C_{1-5}$alkyl-sulfoxyl, nitro, formyl, $C_{1-5}$alkoxycarbonyl and $C_{1-5}$hydroxyalkyl;

$R_3$ is hydrogen or $C_{1-5}$alkyl;

Q represents the group —N($R_4$)($R_5$) wherein $R_4$ and $R_5$ are each independent of each other $C_{1-5}$alkyl or form together with the nitrogen atom to which they are attached a saturated or unsaturated 5- to 6-membered heterocyclic ring optionally containing a second hetero moiety selected from sulfur or =N—($C_{1-5}$alkyl);

Z is O, S or =N($C_{1-5}$alkyl);
m is 0, 1, 2, 3, 4 or 5; r is 0 or 1; s is 2, 3, 4 or 5; in free base or in pharmaceutically acceptable salt form in the therapy of human or veterinary diseases which are caused by bacterial infections.

Within the scope of the present invention, depending on the number of carbon atoms indicated, the term "alkyl" is to be understood as meaning, for example, the following straight-chained and branched groups: methyl, ethyl, n-propyl, isopropyl, n-butyl, sec-butyl, tert-butyl, isobutyl, etc.

"Halogen" signifies chlorine, bromine, fluorine or iodine, preferably chlorine, bromine or fluorine, more preferably chlorine.

The preferred heterocyclic rings are 5- and 6-membered rings that contain one or more heteroatoms selected from nitrogen and sulphur. The more preferred ring contains at least one nitrogen atom.

One group of such heterocyclic rings may contain nitrogen as the sole heteroatom, in particular 1, 2 or 3 nitrogen heteroatoms. Suitable 5- or 6-membered heterocyclic rings containing a single nitrogen atom include pyridine, pyrrole and 4,5-dihydro-3H-pyrrole.

Suitable 5- or 6-membered rings containing 2 nitrogen atoms include imidazole, pyridazine, pyrimidine. Such rings may be fused to, e.g. one or more benzene rings, e.g. to form benzimidazole or perimidine. Suitable 5- or 6-membered heterocyclic rings containing 3 nitrogen atoms include 1,2,4-triazole.

Another group of heterocyclic rings may contain 1 nitrogen atom and 1 sulphur atom, e.g. thiazole, 4,5-dihydrothiazole and benzothiazole. Another group of heterocyclic rings contain 2 nitrogen and 1 sulphur atom, e.g. 1,3,4-thiadiazole.

More preferred within the present invention is the use of compounds of the formula I wherein $R_1$ is ethyl or vinyl; $R_1$ represents the group —S—$C(CH_3)_2$—$CH_2$—NH—C(O)-Q; in which Q represents the group —N($R_4$)($R_5$) wherein $R_4$ and $R_5$ are each independent of each other $C_{1-5}$alkyl or form together with the nitrogen atom to which they are attached a saturated or unsaturated 5- to 6-membered heterocyclic ring optionally containing a second hetero moiety selected from sulfur or =N—($C_{1-5}$alkyl); in free base or in pharmaceutically acceptable salt form.

Even more preferred is the use of compounds of the formula I wherein $R_2$ is represents the group —S—$C(CH_3)_2$—$CH_2$—NH—C(O)—CH($NH_2$)—CH($CH_3$)$_2$; in free base or in pharmaceutically acceptable salt form.

Preferred is also the use of compounds of the formula I wherein $R_1$ is ethyl or vinyl; and Y represents the group —$(CH_2\text{-Z})_r$-$(CH_2)_s$-Q wherein Z is sulfur; r is 1; s is 2; Q represents the group —N($R_4$)($R_5$) wherein $R_4$ and $R_5$ are each independent of each other $C_{1-5}$alkyl or form together with the nitrogen atom to which they are attached a saturated or unsaturated 5- to 6-membered heterocyclic ring optionally containing a second hetero moiety selected from sulfur or =N—($C_{1-5}$alkyl), wherein $R_4$ and $R_5$ are most preferably ethyl; in free base or in pharmaceutically acceptable salt form.

The most preferred compounds are valnemulin and tiamulin; especially valnemulin; in free base or in pharmaceutically acceptable salt form.

The basic antibiotic within the formula I is pleuromutilin (X is OH and $R_1$ is vinyl) which was isolated in 1951 by Kavanagh et al. [Proc. Natl. Acad. Soc. 37, 570–574 (1951)]. Another pleuromutilin derivative of the formula (I), wherein $R_1$ is vinyl and X represents the β,D-xylopranosyl group is described in U.S. Pat. No. 4,247,542. Very typical representatives of the formula I are valnemulin and tiamulin. valnemulin is known under the trade name Econor®, and tiamulin under the trade name Tiamutin®. They have the following chemical structures valnemulin
Y = —C(CH$_3$)$_2$—CH$_2$—NH—C(O)—CH(NH$_2$)—CH(CH$_3$)$_2$
tiamulin
Y = —(CH$_2$)$_2$—N(C$_2$H$_5$)$_2$ Valnemulin in free base form or in physiologically acceptable salt forms is known from e.g. EP-0'153'277, specifically as Example 12 therein, and WO 98/01127. Tiamulin and derivatives thereof and other pleuromutilin derivatives in free base form or in physiologically acceptable salt forms are known from e.g. U.S. Pat. No. 4,032,530, U.S. Pat. No. 4,148,890, U.S. Pat. No. 5,578,585, U.S. Pat. Nos. 4,428,953, 4,060,542, WO 98/01127, and EP-0,153,277.

WO 99/51219 describes the use of pleuromutilin or certain pharmaceutically acceptable derivatives thereof for the manufacture of a medicament adapted for administration to the nasopharynx as a prophylactic treatment of bacterial infections associated with colonization of the nasopharynx. Thus, this reference is directed to the uptake of the active ingredient through the mucous membrane of the upper nasopharynx. In contrast thereo, the present invention is directed to a transdermal uptake of the active ingredient when applied topically to the skin (epidermis) of a patient or the skin or fur of an animal.

The activity spectrum of valnemulin, tiamulin and also other pleuromutilin derivatives is well known and described in the above referenced patents and many scientific papers.

According to the cited references, the compounds of formula I exhibit their antibacterial activity after oral or parenteral administration. The oral treatment, which represent the uptake of the active ingredient through the mucous membrane of the digestive tract, embraces the prophylaxis and the therapy of bacterial infections. In the veterinary field they are preferably administered to domestic animals in foodstuffs or in drinking water.

It has now been found, surprisingly, that the compounds of the formula I are able to penetrate through the skin, meant is here the epidermis, without being metabolized and deactivated. It was absolutely unpredictable that an antibiotic of such a complex chemical structure could pass the skin-barrier and penetrate into the tissue, and reach blood and plasma concentrations that are high enough to control successfully bacterial infections. These bacterial infections embrace systemic infections where the bacteria colonize a smaller or lager portion of the skin. This is one of the exceptional cases where an antibiotic can be applied to the skin instead of being applied for the treatment of systemic infections via a conventional systemic route such as orally or percutaneously. This novel use should not be confused with the conventional cutaneous use of an antibiotic for disinfecting areas of the skin that are infested with the pathogen. The surprise was the fact that the compounds of the formula I have the ability to penetrate through the skin and combat the pathogens inside the animal's body and all over the body.

Representative warm-blooded animal hosts, which may be treated in accordance with the method of the present invention, include humans and preferably domestic animals such as cattle, horses, sheep, goats, poultry, swine, dogs, cats and zoo animals.

This opens a series of new alternatives for treating bacterial infections and especially systemic bacterial infections. These new alternatives may be more convenient and less labour-intensive for farmers and veterinarians than conventional medication with tablets, boli or injections.

Thus the present invention provides a now technique for combating bacterial infections in an animal, comprising applying to the skin of the animal an amount of an antibiotic compound of the formula (I), whereby the compound is absorbed by the animal through its skin (epidermis).

The present technique is preferably applied to mammals especially those which are domestic or farm animals, such as sheep, pigs, calves or cattle, horses, goats, dogs and cats. It may also be applied to human beings. It may be applied also to animals used in laboratories, such as rats, mice and guinea pigs. The compound may be used to prevent or inhibit infection or to treat an infection already present.

In the present technique, the animal absorbs the compound through its skin. The compound is usually applied in a composition containing a physiologically acceptable carrier. A wide range of appropriate carriers may be employed. The composition may be a cream. A liquid composition, however, is particularly convenient to use, e.g. facilitating measuring out doses, and facilitates absorbance through the skin. Thus, a solution or suspension of the compound in a liquid carrier is preferred. Solutions are especially good for transmitting the compound through the skin and are therefore most preferred.

The compounds of the formula I may be formulated for cutaneous/topical administration, for use in veterinary and human medicine, as ointments, creams, lotions, shampoos, powders, sprays (e.g. by a hand spray or in spray races), dips (e.g. in a plunge dip), aerosols, drops (for example, eye or nose drops), pour-ons/spot-ons or by manual methods (e.g. hand-dressing). For administration to farm animals or pets, such as cows, horses, asses, camels, dogs, cats, poultry, sheep, goats, etc., the so-called 'pour-on' or 'spot-on' formulations are especially suitable; these liquid or semi-liquid formulations have the advantage that they only have to be applied to a small area of the pelt or plumage, and, thanks to the proportion of spreading oils or other spreading additives, they disperse by themselves over a larger area, thereby enhancing absorption through the epidermis.

Ointments and creams may, for example, be formulated with an aqueous or oily base with the addition of suitable thickening and/or gelling agents. Ointments for administration to the eye may be manufactured in a sterile manner using sterilized components. Pour-ons and spot-ons may, for example, be formulated for veterinary use in oils containing organic solvents, optionally with formulation auxiliaries for example, stabilizing and solubilising agents. Lotions may be formulated with an aqueous or oily base and will in general also contain one or more emulsifying agents, stabilizing agents, dispersing agents, suspending agents, thickening agents, or coloring agents. Powders may be formed with the aid of any suitable powder base. Drops may be formulated with an aqueous or non aqueous base also comprising one or more dispersing agents, stabilizing agents, solubilising agents or suspending agents. They may also contain a preservative.

Pour-on and spot-on formulations represent a preferred embodiment of the present invention. They are characterized in that the active ingredient is dissolved, emulsified or suspended in a suitable solvent or solvent mixture which is tolerable by the skin, optionally with addition of further auxiliaries, and applied with the aid of a suitable device, e.g. measuring cup or spray bottle to the skin of the animal to be treated.

Pour-on and spot-on technology is well known in the veterinary medicine but primarily in context with the control of ecto- or endoparasites.

It goes without saying that a prophylactic or curative effect can also by achieved by inhalation of the drug. For this purpose the active ingredients of the invention may be delivered for use in human or veterinary medicine in the form of an aerosol spray presentation or an insufflator.

Besides the compound of the formula I and a carrier which is effective for passing the compound through the skin of the animal, the composition may contain additives e.g. to facilitate use on the animal. For example, the composition may contain additives to facilitate contact with the skin of the animal, to protect the skin from any undesirable action e.g. irritation otherwise caused by the carrier, or to improve retention of the composition on the animal.

The viscosity of liquid compositions may be increased over what it would otherwise be, by including thickeners, which increase the viscosity. This may be desirable in order to retard or prevent the composition from running off the animal.

The additives may include for example a surface active agent, an animal fat or wax, e.g. lanolin, a mineral oil, e.g. liquid paraffin, a vegetable oil, e.g. peanut oil, olive oil, corn oil or castor oil, or a polymer, e.g. a hydrocarbon polymer such as polyisobutene.

The surface active agents may comprise anionic compounds for example soaps, fatty sulphate esters such as dodecyl sodium sulphate, fatty aromatic sulphonates such as alkyl-benzene sulphonates or butyl-naphthalene sulphonates, more complex fatty sulphonates such as the amide condensation product of oleic acid and N-methyl taurine or the sodium sulphonate of dioctyl succinate.

Compared with oral treatment or injection treatment, pour-on and spot-on formulations offer distinct advantages which are of great importance in veterinary practice. As typical advantages may be mentioned:

1) greater ease of handling;
2) all animals of a herd can easily be medicated;
3) the danger of injury to animals and the person giving the treatment is reduced;
4) the danger of transmission of injection diseases is considerably reduced;
5) the local intolerance phenomena are substantially less than in case of injections; and
6) the expenditure on apparatus in production is lower.

The action of formulations administered orally or in case of injection treatment is usually more pronounced than in case of the corresponding pour-on or spot-on application. However, taking into account the above listed advantages one can put up with this less pronounced action. To reach a comparable efficacy as in the case of oral or percutaneous treatment the total amount of active compound of the formula I can be increased without causing undesirable effects.

Within the present invention tiamulin and especially valnemulin represent the most preferred active ingredients for antibiotic pour-on and spot-on formulations in the prophylaxis or therapy of bacterial, and preferably systemic bacterial infections, wherein the treatment comprises the penetration of a bactericidally effective amount of a compound of the formula I through the skin (epidermis).

The compounds of the formula I may be also administered in combination with other suitable pharmaceutically active ingredients to broaden the spectrum of activity. The totall dosage may vary for the same active ingredient from one species of animal to another as well as within a species of animal, since it depends inter alia on the weight and the constitution of the animal. The total daily dosages of the compounds of the invention employed in both veterinary and human medicine will suitably be in the range 0.01–2000 mg/kg body-weight, preferably from 0.1–1000 mg/kg body-weight, more preferably from 1–100 mg/kg and these may be administered as single or divided doses. However, they can also be administered weekly, monthly or at even longer intervals. In such cases the dosage will be much higher than the daily one and has to be adapted to the administration form, the body weight and the concrete indication. The appropriate dosage can be determined by conducting model tests, preferably via animal models. The most suitable interval for administration must be determined on a case-by-case basis.

Generally such formulations will include the compound in association with a suitable carrier or diluent. Such carriers may be liquid or solid and designed to aid the application of the compound either by way of dispersing it where it is to be applied or to provide a formulation, which can be made by the user into a dispersible preparation. Such formulations are well known in the art and may be prepared by conventional methods such as, for example, by blending and/or grinding of the active ingredient(s) together with the carrier or diluent, for example, solid carrier, solvent or surface active agent.

Suitable solid carriers, for use in formulations such as dusts, granulates and powders may be selected from, for example, natural mineral fillers, such as diatomite, talc, kaolinite, montmorillonite, prophyllite or attapulgite. Highly dispersed acid or highly dispersed absorbent polymers may, if desired, be included in the composition. Granulated adsorptive carriers, which may be used, may be porous (such as pumice, ground brick, sepiolite or bentonite) or non-porous (such as calcite or sand). Suitable pregranulated materials, which may be used, may be organic or inorganic including dolomite and ground plant residues. Suitable solvents for use as carriers or diluents include but are not limited to: aromatic hydrocarbons, aliphatic hydrocarbons, alcohols and glycols or ethers thereof, esters, ketones, acid amides, strongly polar solvents, optionally epoxidized vegetable oils and water. Conventional non-ionic, cationic or anionic surface-active agents, for example, ethoxylated alkyl phenols and alcohols, alkali metal or alkaline earth metal salts of alkyl benzene sulphonic acids, lignosulphonic acids or sulphosuccinic acids or sulphonates of polymeric phenols which have good emulsifying, dispersing and/or wetting properties may also be used either alone or in combination in the compositions.

Stabilizers, anti-caking agents, anti-foaming agents, viscosity regulators, binders and adhesives, photostabilisers, as well as fertilisers, feeding stimulants or other active substances may, if desired, be included in the compositions. The compounds of the invention may also be formulated in admixture with other therapeutically active compounds. In the formulations, the concentration of active material is generally from 0.01 to 99% and more preferably between 0.01% and 40% by weight. Commercial products are generally provided as concentrated compositions to be diluted to an appropriate concentration, for example from 0.1 to 0.01% by weight, for use.

It has also surprisingly been found that the compounds of the formula I in freebase form or in pharmaceutically acceptable salt form exhibit an excellent activity against (stable footrot) digital dermatitis which is common in farm animals such as sheep, goats, horses, but particularly dairy cows, and beef cattle. They also show an excellent activity against digital pododermatitis, or footrot, principally of sheep, which is generally a chronic inflammation of the skin in the area between the toes of the feet (digital cleft). This infection is caused by the bacterium *Dichelobacter nodosus*. The skin in the area of the digital cleft will appear puffy with a dry exudation, which will cause a crust to form. The condition may occasionally cause lameness or heel crack/heel erosion but generally results in an alteration in the animal's gait. Secondary infection with *Fusobacterium necrophorum* is usual and results in under-running of the hoof, with resulting severe lameness.

Digital necrobacillosis (digital phlegmon, foul-in-the-foot, clit-ill etc.) is an acute infectious disease of hoofed animals, especially cattle. This disease is characterized by swelling and lameness in one or more feet. It can become chronic if treatment is not provided or is delayed. It is caused by the bacterium *Fusobacterium necrophorum*. Other organisms such *Bacteroides melaninogenicus* may be involved. Both organisms are nonmotile, anaerobic, gram-negative bacteria that are routinely cultured from lesions. However, *Fusobacterium necrophorum* is capable of causing footrot by itself when experimentally injected into the skin of the digital space. *Bacteroides nodosus*, the agent causing ovine footrot, may also be involved. Digital necrobacillosis is characterized by a sudden onset of mild to severe lameness with swelling of the coronet and digital space. The digital space is often necrotic and fissured, with a characteristic foul odor but little exudate. Body temperature is often elevated, appetite reduced, and body condition lost. Affected animals are often inappetant, and gazing is reduced in pastured animals. Breeding bulls are incapacitated, especially if a hind foot is involved.

Digital dermatitis, principally of dairy cattle, is a disease, which has been recently recognised. Its aetiology is uncertain but a spirochaete, perhaps in association with other bacteria, is thought to be causally involved. It is characterised by superficial inflammation of the digital skin, especially at the heel, and results in lameness and reduced milk yield.

Said infectious diseases of the hoof are common in most countries and are the most common causes of lameness. Morbidity varies from one or two animals in a herd or pen to explosive outbreaks with very high morbidity. The diseases are seen year round. All ages are susceptible, but the diseases are most commonly seen in animals of weaning age and older. The same animals may be affected repeatedly. Digital dermatitis, digital pododermatitis, and digital necrobacillosis have in the past erroneously been mentioned as interdigital dermatitis, interdigital pododermatitis, and interdigital necrobacillosis.

It has now surprisingly been found that the administration of a compound of the formula I in freebase form or in pharmaceutically acceptable salt form leads to a fast response to the treatment and in rapid healing and do not cause any problem with regard to the milk. In early cases one treatment is sufficient. In severely advanced cases, where the organism penetrates to adjacent tendon sheaths, joint capsules, and/or bone a repeated treatment can be necessary. Preventive measures can easily be managed by using footbaths containing one or more of the compounds of the formula I in freebase form or in pharmaceutically acceptable salt form.

Thus, a further objective of the present invention is to provide an antibacterial composition for the prevention or treatment of infectious diseases of the foot, preferably those that are caused by one or more bacteria selected from the group consisting of *Dichelobacter nodosus, Fusobacterium necrophorum, Bacteroides nodosus* and *Bacteroides melaninogenicus*, which composition comprises as active ingredient a compounds of the formula I in free base or in pharmaceutically acceptable salt and a physiologically acceptable carrier. The composition and method of the present invention are effective under a wide variety of conditions and dilutions. The composition of the present invention may also comprise other additives, which may be any substance that enhances the composition with regard to improved solubility or dispersion of other components, improved adhesion of the composition to the affected hoof area, control of wetting characteristics, and improved stability, which may be related to such properties as surface tension and viscosity, among other properties. The composition of the present invention may also comprise colorants, to provide a composition that is visible when applied, to ensure proper and complete application.

The compounds of the formula I in freebase form or in pharmaceutically acceptable salt form can be administered via different routs, for example, coutaneously or systemically. The coutaneous administration is mostly preferred. Consequently, the present invention encompasses a method for the prevention or treatment of infectious diseases of the hoof in animals, comprising coutaneously administering the antibacterial composition of the present invention preferably at or near the infected area. More preferably, the composition is used to treat footrot. The composition may be applied by pouring, squirting, flushing, sponging, or spraying it on or near the infected area, or by incorporating in a footwrap. In a preferred embodiment, the compositions of the present invention are applied by spraying. Alternatively, the animal's hoof may be soaked, submerged, or immersed in the claimed compositions to effect treatment.

From the above description, one skilled in the art can easily ascertain the essential characteristics of the present invention, and without departing from the spirit and scope thereof, can make various changes and modifications of the invention to adapt it to various utilities and conditions. Thus other embodiments are also within the claims.

Without further elaboration, it is believed that one skilled in the art can, based on the description herein, utilize the present invention to its fullest extent. The following specific example is, therefore, to be construed merely as illustrative, and does not limit the remainder of the disclosure in any way whatsoever. Publications mentioned herein are hereby incorporated by reference.

The following examples of preparation and application serve to explain the invention without limiting it to the individual aspects of these examples.

Formulation Examples
Dusts:

| | |
|---|---|
| Valnemulin: | 0.1 to 10%, preferably 0.1 to 1% |
| Solid carrier: | 99.9 to 90%, preferably 99.9 to 99% |

Suspension concentrates:

-continued

| | |
|---|---|
| Valnemulin: | 5 to 75%, preferably 10 to 50% |
| Water: | 94 to 24%, preferably 88 to 30% |
| Surfactant: | 1 to 40%, preferably 2 to 30% |
| Slow Release Formulation: | |
| Valnemulin: | 0.1–1.0 g |
| Groundnut oil: | ad 100 ml |
| or | |
| Valnemulin: | 0.1–1.0 g |
| Sesame oil: | ad 100 ml |

Preparation: The active ingredient is dissolved in part of the oil with stirring and where appropriate gentle healing, then made up to the desired volume and sterile-filtered through a suitable membrane filter with a pore size of 0.22 µm.

Solutions:
- 15% valnemulin in 2,2-dimethyl-4-hydroxy methyl1-1,3-dioxolane
- 10% valnemulin in diethylene glycol monethyl ether
- 10% valnemulin in polyethylene glycol (mol. wt. 300)
- 5% valnemulin in glycerol

| Pour-on/Spot-on: | (i) | (ii) | (iii) | (iv) |
|---|---|---|---|---|
| valnemulin | 10.65 g | 10.65 g | 10.65 g | 21.00 g |
| Liquid parafin of high viscosity | — | 10.00 g | — | — |
| Vegetable oil | — | — | — | 30 ml |
| Isopropyl myristate | — | — | 10.00 g | — |
| Trimethyl benzenes | — | — | — | 10.00 g |
| Isopropanol | add 100 ml | add 100 ml | add 100 ml | add 100 ml |

Biological Examples

1. Preliminary Test: Transdermal Study in Pigs

| | |
|---|---|
| Test animals: | pigs (animal no 1 & animal No 2) |
| Test formulation for animal no 1: | water solution containing 10% valnemulin |
| Test formulation for animal no 2: | 40% ethanol/water solution containing 10% valnemulin |
| Test dosage: | 2 × 25 mg/kg of body weight |

The test solution is administered cutaneously to the skin of the animal and the river, lung, skin, bile and plasma concentrations are determined. The results are presented in Table 1.

TABLE 1

| | Animal No 1 | Animal No 2 |
|---|---|---|
| liver | 0.175 | 0.132 |
| lung | 0.916 | 0.353 |
| skin | 39.056 | 6.965 |
| bile | 0.155 | <limit of detection |
| plasma 3 hours after 1st application | <limit of detection | <limit of detection |
| plasma 6 hours after 1st application | <limit of detection | 0.07 |

For determining the concentrations (µg/ml of plasma or g of tissue) a calibration curve of valnemulin in plasma is used. These investigations are not meant to determine the exact values but to provide only a yes or no answer. They demonstrate the transdermal potential of the tested product.

2. Assessment of the Systemic Absorption of Valnemulin-Type of Compounds After Cutaneous Administration in Cattle Disease: Footrot Type of administration: Footbath or directly as spray Test Protocol: Four lactating adult cows with clinical signs of Bovine Digital Dermatitis are recruited to the study. Blood and milk samples are taken before, and at intervals after application of a water/ethanol solution containing 10% valnemulin either as a footbath, or directly by spraying the feet.

Test Formulation: Water/ethanol solution containing 10% valnemulin

| | |
|---|---|
| valnemulin | 10.65 g* |
| p-hydroxybenzolcacid propylester | 0.02 g |
| p-hydroxybenzolcacid methylester | 0.18 g |
| Ethanol | 5.00 g |
| Water (purified) added to make | 100 ml |

*Initial weight based on a content of 93.9% valnemulin (base)

Footbath solutions are prepared fresh each treatment day. A calculated quantity of test product is added to an estimated volume of water, which is placed in the footbath beforehand.

The cows are driven individually into the footbath and made to stand there with their feet covered by footbath solution for 2 minutes.

Foot spraying involves the use of a hand operated spraying device into which 100 ml of the test product are placed. Said 100 ml are distributed between the feet of each cow and applied directly to the lower leg areas and around and underneath each foot.

Valnemulin content of samples is determined by a validated High Performance Liquid Chromatography (HPLC) method. Day 1; a.m. milking samples (50 ml/sample) are taken before the first treatment, thus serving as control measurements. Blood samples (20 ml/sample) are taken from the coccygeal vein of each cow on eleven occasions during trial.

Schedule of Treatments (D=Day) (a.m.=morning; p.m.=afternoon)

Day (D) 1 Individual treatment by standing in a 150–200 L footbath containing valnemulin as a 10% solution at a rate of 3 liters per 100 liters water.

Day (D) 3 Individual treatment by standing in a 150–200 L footbath containing valnemulin as a 10% solution at a rate of 3 liters per 100 liters water.

Day (D) 5 Affected and healthy feet were sprayed with 25 ml of a water solution containing 10% valnemulin.

Blood samples are taken before the first treatment and at the stated hours after subsequent treatments. Milk samples are taken at the time of treatment and at subsequent milkings. Valnemulin concentrations are surprisingly found in most milk and blood samples. The compound has obviously the ability to penetrate through the skin. There is no correlation between severity of lesions and blood or milk concentrations. After one week none of the treated cows shows any symptoms of footrot.

Additional experiments in pigs and cattle show that after topical application of valnemulin as a spot on fairly high amounts of the active ingredients are found in many tissues, for example, in brain, liver, muscle, spleen, and lung.

What is claimed is:

1. A method for transdermally controlling a bacterial infection in a non-human animal comprising the step of topically applying to said non-human animal a medicament comprising valnemulin in free base or in pharmaceutically acceptable salt form.

2. The method according to claim 1 wherein said medicament is in the form of a pour-on spot-on, dip or spray.

3. The method according to claim 1 wherein the method is used for the prevention or treatment of bacterial diseases of the foot of a hoofed animal.

4. The method according to claim 1 wherein the method comprises a) the cutaneous administration of the medicament containing valnemulin in free base or in pharmaceutically acceptable salt form, and b) the penetration of valnemulin through the skin.

5. A method for producing a transdermally applied medicament for the prophylactic or therapeutic treatment of a bacterial disease of the foot of a hoofed animal, which comprises preparing a composition containing valnemulin in free base or in pharmaceutically acceptable salt form and a carrier or diluent or both.

6. Transdermal treatment of bacterial infections in non-human animals comprising the administration of valnemulin in free base or in pharmaceutically acceptable salt form to the skin or fur of said non-human animal in need of treatment thereof.

7. A method for controlling a bacterial disease of the foot of a hoofed animal comprising the step of topically applying to said hoofed animal valnemulin in free base or in pharmaceutically acceptable salt form.

8. The method according to claim 7, wherein said bacterial disease is caused by one or more bacteria selected from the group consisting of *Dichelobacter nodosus, Fusobacterium necrophorum, Bacteriodes nodosus* and *Bacteriodes melaninogenicus.*

9. The method according to claim 7, wherein said bacterial disease is interdigital dermatitis, interdigital pododermatitis, or interdigital necrobacillosis.

* * * * *